United States Patent [19]

DuBois et al.

[11] Patent Number: 5,430,225
[45] Date of Patent: * Jul. 4, 1995

[54] METHODS OF PRODUCTION OF NOVEL MOLYBDENUM-SULFIDE DIMERS AND REACTIONS OF THE SAME

[75] Inventors: Mary R. DuBois; Richard D. Noble, both of Boulder; Carl A. Koval, Lafayette, all of Colo.

[73] Assignee: The University of Colorado Foundation, Inc., Boulder, Colo.

[*] Notice: The portion of the term of this patent subsequent to May 9, 2012 has been disclaimed.

[21] Appl. No.: 112,845

[22] Filed: Aug. 26, 1993

Related U.S. Application Data

[62] Division of Ser. No. 750,045, Aug. 27, 1991, Pat. No. 5,391,791.

[51] Int. Cl.$^6$ .......................... C07C 7/00; C07C 7/17
[52] U.S. Cl. .................................... 585/855; 585/856; 585/865; 585/818
[58] Field of Search ................ 585/855, 856, 865, 818

[56] References Cited

PUBLICATIONS

McKenna et al., *Synthesis of Inequivalently Bridged Cyclopentadienyl Dimers of Molybdenum and a Comparison of Their Reactivities with Unsaturated Molecules and with Hydrogen*, 105 J. Am. Chem. Soc'y 5329–5337 (1983).

Primary Examiner—Asok Pal
Assistant Examiner—Nhat D. Phan
Attorney, Agent, or Firm—Swanson & Bratschun

[57] ABSTRACT

Derivatized molybdenum-sulfide dimers of the general formula $[(C_5R_5Mo)_2(\mu\text{-}S)_{4-x}(\mu\text{-}SR)_x]^n$ are utilized in the solid state, incorporated in permselective membranes and in aqueous solution as chemical specific complexing agents in various separation processes.

16 Claims, No Drawings

METHODS OF PRODUCTION OF NOVEL MOLYBDENUM-SULFIDE DIMERS AND REACTIONS OF THE SAME

This is a divisional of application Ser. No. 07/750,045, filed on Aug. 27, 1991, now U.S. Pat. No. 5,391,791.

FIELD OF THE INVENTION

This invention describes a variety of novel molybdenum-sulfide dimer compounds. These dimer compounds are characterized by their ability to reversibly bind alkenes and/or their ability to react with alkynes. Based on various alterations of the basic molybdenum-sulfide dimer structure, the dimers of the present invention exhibit varying useful properties such as water solubility and ligand reactivity. Also included in this invention are processes that use the molybdenumsulfide dimer compounds in olefin separation and acetylene removal processes.

BACKGROUND OF THE INVENTION

In a series of related papers, M. Rakowski DuBois and co-workers have described the existence of a novel class of molybdenum-sulfide dimer compounds. See, e.g., M. Rakowski DuBois et al., *J. Am. Chem. Soc.*, vol. 101, pp. 5245–5252 (1979); M. Rakowski Dubois et. al., *Inorg. Chem.*, vol. 20, pp. 3064–3071 (1981); M. McKenna et al., *J. Am. Chem. Soc.*, vol. 105, pp. 5329–5337 (1983); and J. Birnbaum et al., *Organometallics*, vol. 10, pp. 1779–1786 (1991). The dinuclear sulfide bridged molybdenum dimers have the general formula $[(C_5H_5Mo)_2(\mu\text{-}S)_{4-x}(\mu\text{-}SR)_x]^n$, where $x = 0-3$, and $n = 0$, $+1$, $-1$.

Surprisingly, it has been shown that these molybdenum-sulfide dimers will undergo reversible interactions with olefins. Of course, the reversible interactions of olefins with a variety of transition metal ions has been known for many years. For example, Ag(I) binds reversibly with olefins. However, the reactions of these dimers with olefins is fundamentally different from those characterized for silver and other metal ions because it is the sulfide ligands of the molybdenum-sulfide dimers that act as the site of olefin binding. A typical reaction is shown below.

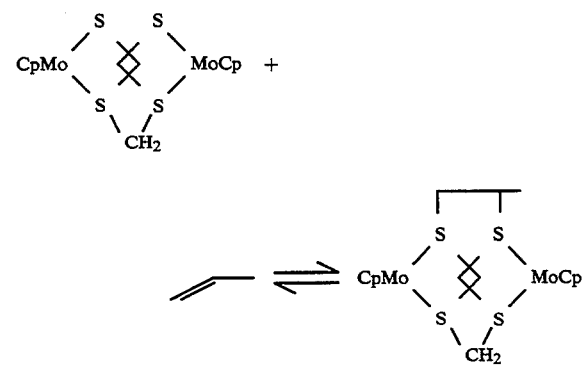

A series of experiments were performed to determine the equilibrium constants for the above reaction in chloroform for a series of olefins. See, McKenna Supra. The data indicate that some of the binding constants are in the same range as those observed for olefin binding to the silver ion. It was also shown that the equilibrium constants were quite sensitive to the steric and electronic features of the olefin. For example, the equilibrium constant for trans-2-butene at 26° C. was found to be $(3\pm 1)\times 10^2$ while cis-2-butene was $17\pm 2$ and cis-2-hexene was $3.9\pm 0.2$.

In addition to its reactivity to olefins, the molybdenum-sulfide dimers of Rakowski Dubois have also been shown to form irreversible adducts with acetylene to yield thermally stable alkenedithiolate compounds as shown in a typical example below.

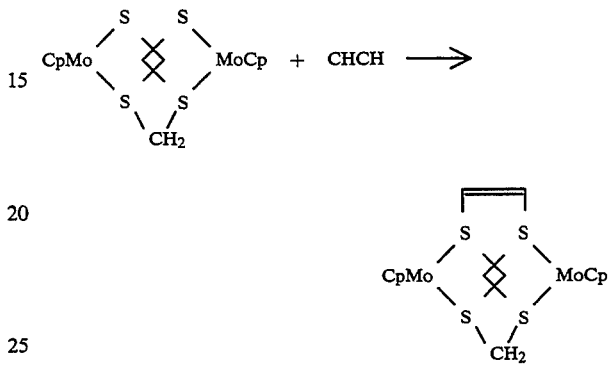

Although the alkenedithiolates formed are considerably more stable than the molybdenum-sulfide olefin adducts, they are not unreactive. See, McKenna supra. For example, exchange reactions between certain alkenedithiolates and various alkynes have been detected. It has also been shown that the alkenedithiolates can be hydrogenated under mild conditions to yield the original molybdenum-sulfide dimer and the cis-alkene as shown below:

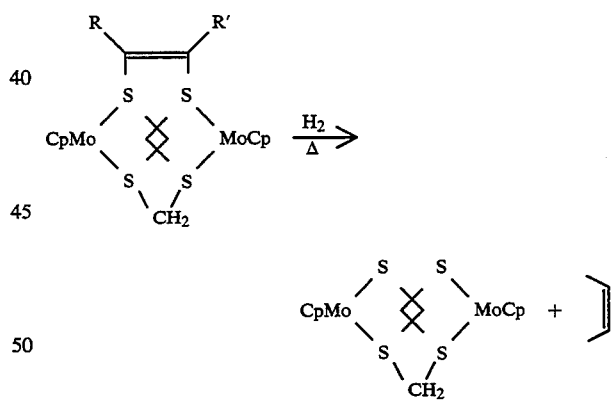

Under the mild reducing conditions employed, the alkanedithiolate moiety of the dimer (in the example, the methylene dithiolate) is not reduced.

In a few instances, the ability of metal ions to bind reversibly to olefins has been utilized in olefin separation and purification systems. For example, olefin adducts of Ag(I) ion have been used in chromatographic systems for the separation of olefins. More recently, aqueous silver nitrate solutions have been used to separate ethylene or propylene from purified multicomponent gas streams. See, U.S. Pat. No. 4,174,353 of Marcinkowsky et al. A major concern when utilizing the silver/olefin adduct chemistry, is that the silver ion forms a complex with acetylene which is explosive when dry and rigorous methods must be employed to remove acetylene from any gas stream that will come in contact with the silver ion. A further problem associated with silver/olefin separation schemes, is that the silver ion is rapidly poisoned by H₂S, a common impurity in gas associated with the thermal cracking of hydrocarbons.

In contrast to the use of metal ion chemistry in olefin separation schemes, the molybdenum-sulfide dimers are unaffected by the presence of H₂S. In addition, the inventors of the present invention have also described how the ability of the molybdenum-sulfide dimers to bind and to subsequently reduce alkynes may be used in alkyne removal processes.

Prior to the conception of this invention, molybdenum-sulfide dimers had not been developed for use in any way other than as an interesting and unique chemical compound. For example, the molybdenum-sulfide dimers reported to date have not been water soluble, and the olefin alkene adduct reactions have only been studied in chloroform or other organic solvents.

One of the primary features of the present invention is the separation or purification of olefin streams. Olefins are generally produced via catalytic cracking processes. Such processes produce refinery-grade olefins (65-70% purity). Currently, refinery grade olefins are further separated and purified using distillation columns to produce polymer-grade olefins (99.5% purity) or chemical-grade olefins (95% purity). Frequently two distillation columns must be employed. Each distillation step is expensive and energy intensive, and even incremental gains in purity greatly increase the costs of the olefin products.

Current theories for improving the economies of olefin separations and purifications suggest that a hybrid separation process be utilized. In addition to the conventional distillation step, some other chemically specific process would be utilized to enhance olefin purity for greatly reduced costs. Processes that have been suggested as potentially being amenable to the hybrid approach are the following: 1) a facilitated transport membrane using a chemically-specific complexing agent; 2) absorption/stripping with a chemical solvent; and 3) adsorption/desorption on a solid support.

The rationale for the use of hybrid olefin separation processes is as follows: conventional separation technology can only achieve a certain level of separation per stage. This level of separation is not a constant for each stage. As higher purity levels are required, the number of stages increases rapidly. This also means a dramatic increase in the costs for additional processing equipment. On the other hand, a separation step using reversible chemical complexation obtains improved selectivity at the same time that the driving force of conventional olefin separation processes decreases. Although this is not intuitive, it occurs because there is a large excess of complexing agent present and the selective reaction becomes very efficient. The hybrid process, therefore, typically combines a conventional separation process to achieve a certain level of purity and follows it with a separation step using reversible chemical complexation to "polish" or further purify the desired product. See, Haggin, Chem. & Eng. News., pg. 23-24 Feb. 25, 1991.

The present inventors have recognized the potential the molybdenum-sulfide dimers have as part of a hybrid olefin separation process. Previous reversible binding systems have used $AgNO_3$ or copper compounds as complexing agents. As described above, $AgNO_3$ reacts irreversibly with sulfur compounds. Copper compounds are very susceptible to reactions with oxygen, water or sulfur compounds. Such reactions lead to very poor lifetimes in operation or, in the alternative, lead to the higher costs required for removing the compounds prior to separation and purification. Similar problems exist with acetylene (when purifying ethylene) and propyne (when purifying propylene). Again, the alkyne impurities increase costs either by greatly reducing the lifetime of the complexing agent, or by the mechanism required to remove the alkyne prior to the separating process utilizing the complexing agent.

Acetylene removal typically may be accomplished in a variety of manners. In one process, the gaseous feed stream is passed through a chilled polar solvent such as dimethyl formamide (DMF). A pressure swing is then used to recover the acetylene. Another method is the dehydrogenation of the acetylene over a noble metal catalyst.

The present invention describes .modified molybdenum-sulfide dimers having characteristics that will allow this unique family of compounds to be used in a variety of processes, including alkene separation/purification processes.

SUMMARY OF THE INVENTION

The present invention includes, most fundamentally, the utilization of a class of molybdenum-sulfide dimer compounds in olefin separation/purification processes and for the complexation and subsequent reduction of alkynes.

Included herein are molybdenum-sulfide dimer compounds of the general formula $[(C_5R_5Mo)_2(\mu-S)_{4-x}(\mu-SR)_x]^n$ where $x=0-3$, and $n=0, +1, -1$, that are modified to be used in commercially viable processes. Modifications of the dimers include chemical modifications such as the synthesis of water soluble dimers and dimers containing functionally reactive ligands that can be used to incorporate the dimer within the matrix of polymeric materials. Modifications also include supporting the molybdenum-sulfide dimer on solid supports. In one embodiment of the invention, the dimer is supported in an ion-exchange membrane.

Due to the novel formulations/modifications of the molybdenum-sulfide dimers, the reversible complexation with olefins and the irreversible complexation with alkynes have been shown to be functional in the aqueous phase, in solid state reactions, and within a membrane matrix.

The advantages of having olefin complexing agents in aqueous solution have to do with the fact that olefins have a much lower solubility in water than in organic solvents. The total amount of olefin in solution is based on physical solubility—which is usually a poor separation criteria—and the quantity of olefin bound to the complexing agent. .Reducing the physical solubility increases the chemical specifity of the solution, and therefore, the selectivity of the separation process.

The complexing agents in solution can be used in either a direct gas-liquid contactor or a membrane separation device. Gas-liquid contacting can be accomplished via packed columns, open columns or by various staging approaches. In a membrane separation device, separate phases are maintained on opposite sides of a permselective membrane. Mass flow of the olefin in the first solution occurs across the membrane and the second solution is enriched in the olefin that is selected for by the complexing agent incorporated into the membrane.

In another embodiment using membrane separations, the membrane may serve as a permselective barrier between feed or receiving phases and the solution contains the complexing agent. The solution may or may not "wet" the membrane and enter the pores of the membrane. This embodiment is normally termed a membrane contactor.

Gas phase/solid phase separations can be performed when utilizing the supported molybdenum-sulfide dimers of the present invention. Such separations will generally be accomplished on a column.

The separations that are included within the scope of this invention by use of the molybdenum-sulfide dimers include the separation of olefins from alkanes (e.g., ethylene from ethane, propylene from propane), the separation of alkenes (e.g., ethylene from propylene), the separation of olefin isomers (e.g., cis-2-butene from trans-2-butene), the separation of olefins from alkynes (e.g., propylene from propyne) and the removal of acetylene from a gaseous hydrocarbon feed stream. In a further embodiment of the invention, the molybdenum-sulfide dimers are "catalytic" in the reduction of alkynes.

The various aspects of the invention are described in more detail below.

DETAILED DESCRIPTION OF THE PREFERRED EMBODIMENTS

This invention describes the use of a unique class of inorganic compounds in olefin separation/purification processes and for alkyne removal or reduction processes. The unique class of inorganic compounds is defined by their ability to reversibly bind olefins and to more tightly bind alkynes. In the preferred embodiments of the invention, the inorganic compounds are molybdenum-sulfide dimer compounds of the following general formula: $[(C_5R_5Mo)_2(\mu-S)_{4-x}(\mu-SR)_x]^n$, where $x=0-3$, and $n=0, +1, -1$. This core structure can be depicted as follows for $x=2$ and $n=0$:

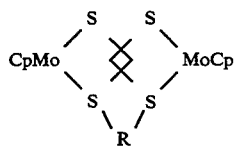

In various embodiments of the invention, this core molybdenum-sulfide dimer structure can be modified in a limited number of ways. Substitutions can be made to the alkanedithiolate moiety R or to the cyclopentadienyl moieties Cp.

The various derivatives—many of which are water soluble or may be easily made water soluble—of the molybdenum-sulfide dimer retain their ability to reversibly bind alkenes and to form alkenedithiolate compounds upon reaction with alkynes. As discussed below, these properties, in conjunction with their water soluble properties, enables the use of such materials in various alkene separation/purification processes.

In an additional embodiment of the present invention, it is desired that the molybdenum-sulfur dimer be a polymer precursor. In one preferred embodiment of the molecule having this type of functionality $Cp=C_5H_4CHCH_2$. Various specific embodiments of the modified molybdenum-sulfide dimers of the present invention are given in TABLE 1.

TABLE 1

| R | $C_p$ | Property |
|---|---|---|
| —CH—CO$_2$Na | C$_5$H$_5$ | water solubility |
| —CHC(CH$_3$)$_2$CO$_2$Et | C$_5$H$_5$ | water solubility |
| —CHC(CH$_3$)$_2$CO$_2$Li | C$_5$H$_5$ | water solubility |
| —CHCH(CO$_2$CH$_3$)$_2$ | C$_5$H$_5$ | water solubility |
| —CH$_2$ | C$_5$H$_4$CO$_2$CH$_3$ | water solubility |
| —CH$_2$ | C$_5$H$_4$CO$_2$Na | water solubility |
| —CH$_2$ | C$_5$H$_4$CONH(CH$_2$)$_x$NHR$_2$+ | water solubility |
| —CH$_2$ | C$_5$H$_4$CHCH$_2$ | prepolymer |

Additional embodiments of the derivitized molybdenum-sulfide dimers of the present invention have the general structure:

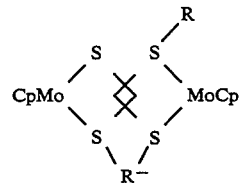

In one such embodiment, $R'=CH(CH_3)CO_2H$. Such derivatives are also more soluble in water than the base dimer.

The present invention is not, however, limited to the modified members of the molybdenum-sulfide dimer family listed in Table 1. Compounds that are homologous to the listed dimers, specifically those that can be prepared generally according to the procedures as described in Examples 1 and 2 below, are included within the scope of this invention.

Water soluble molybdenum-sulfide dimer, therefore, is hereby defined to include all compounds containing molybdenum and sulfur capable of forming chemically- or thermally-reversible alkanedithiolate or alkenedithiolate complexes that have significant solubility in water or aqueous solvents.

The water soluble molybdenum-sulfide dimers of the present invention have been shown to form complexes with olefins. The equilibrium constant for the following reaction has been determined.

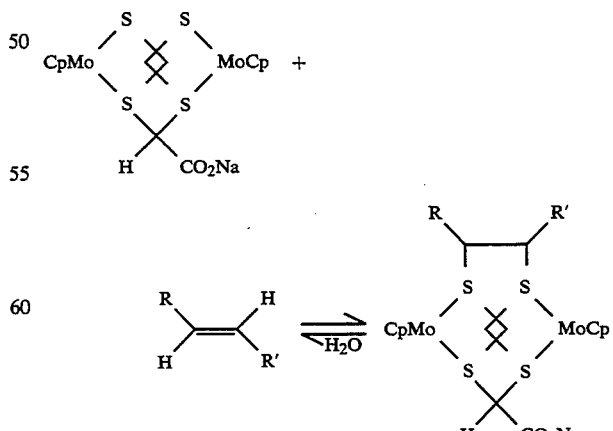

For the above reaction the equilibrium constants for $R=H$, $R'=CH_3 K=4200$ and for $R=R'=CH_3 K=245$.

Experimental details of these experiments are set forth in Example 3 below.

Additional equilibrium constants for a wide variety of water soluble molybdenum-sulfide dimers are shown in Table II below. For certain cases, the olefin complexation reactions were carried out in either aqueous or non-aqueous solutions in the presence of about one equivalent of H2S per equivalent of dimer. No inhibition of the olefin binding is detected in the presence of H2S.

TABLE II

| Complex (Solvent) | Olefin | $K_{eq}$ at 25° C. $(M^{-1})$ |
|---|---|---|
| CpMo(S S)(S S)MoCp CH2 (CDCl3) | Ethene | >10⁴ |
| | Propene | >10⁴ |
| | t-2-Butene | 1.4 × 10³ |
| | c-2-Butene | 17 |
| | c-2-Hexene | 4 |
| | Styrene | 90 |
| | c-Stilbene | <1 |
| MeCpMo(S S)(S S)MoCpMe CH2 (CDCl3) | Ethene | >10⁴ |
| | Allene | >10⁴ |
| | Propene | 1200 |
| | 1-Butene | 460 |
| | c-2-Butene | 20 |
| | t-2-Butene | 450 |
| | Isobutene | 5 |
| | Styrene | 10 |
| C5Me5Mo(S S)(S S)MoC5Me5 CH2 (CDCl3) | Ethene | 150 |
| MeCpMo(S S)(S S)MoCpMe CH(CO2Me) (CDCl3) | Ethene | 42,200 |
| | Propene | 1,500 |
| | 1-Butene | 600 |
| | t-2-Butene | 220 |
| | Styrene | 20 |
| CpMo(S S)(S S)MoCp CH(CO2Na) (D2O) (CD3OD) | Ethene | 10⁴ |
| | Propene | 4,200 |
| | t-2-Butene | 245 |
| | Styrene | 60 |
| [CpMo(S S)(S S)MoCp]SO3CF3 CMe3 CH2 (CD2Cl2) | Ethene | 95 |
| | Propene | 5 |

In Example 5, procedures are described for demonstrating the effectiveness of molybdenum-sulfide dimers, specifically water soluble molybdenum-sulfide dimers, as olefin transport agents in an aqueous liquid membrane. The molybdenum-sulfide dimers of the present invention may be utilized in a variety of separation processes in order to achieve the variety of useful chemical separations to which they may be capable of performing. The separation processes include liquid/liquid, gas/liquid, liquid/solid and gas/solid procedures that are familiar to those skilled in the art.

As described above, chemically-specific agents incorporated into membranes can be used in olefin separation/purification processes. (By membrane transport action, the complexed olefin will migrate within, and be released on, the other side of the membrane.) In one non-limiting embodiment of the present invention, a molybdenum-sulfide dimer of the invention is made part of a membrane. Preferably, the dimer is a water soluble molybdenum-sulfide dimer, and the membrane is an aqueous liquid membrane. This method can also be used with a cast polymer film.

The membrane contactor can be used in a variety of ways to affect-alkene purification/separation. In a non-limiting example, a feed gas stream containing relatively high purity propylene, contaminated with propane (and/or high molecular weight alkenes) is introduced into one side of the membrane contactor. The liquid stream on the opposite side of the membrane will be enriched in propylene relative to the feed stream. This is due to the relative specificity of the dimer to complex with the propylene in preference to the other components of the feed stream.

In another embodiment of the present invention, feed gas streams containing mixtures of olefins, e.g., cis and trans 2-butene, may be separated by the ability of the membrane supported molybdenum-sulfide dimer to preferentially bind and transport trans-2-butene.

The present invention also includes the membranes supporting the molybdenum-sulfide dimers. In one embodiment of the present invention, and as described in Example 5 below, cationic molybdenum-sulfur dimers are incorporated into ion exchange membranes. In a preferred embodiment, ion exchange membranes referred to as NAFION ion exchange membranes (NAFION is a registered trademark of E. I. du Pont Ne Mours & Co.) of varying thickness are used to support the molybdenum-sulfide dimers. Up to 80% of the available ion exchange sites within the ion exchange membranes may incorporate molybdenum-sulfide dimers of the present invention. In preferred embodiments, the ion exchange membranes are loaded to between 10 and 80% of capacity with the molybdenumsulfide dimer $[C_5H_5Mo)_2(S_2CH_2)(\mu-S)(\mu-SCMe_3)]^+$. In an alternate embodiment, anionic molybdenum-sulfur dimer

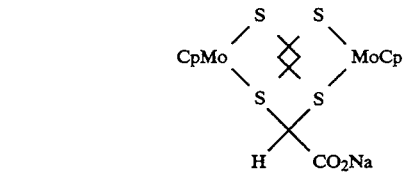

may be loaded onto an anionic ion exchange membrane, for example RAIPORE anion exchange membrane. (RAIPORE is a registered trademark of The Electrosynthesis Co.)

The modified monomer (or prepolymer) derivatives of the molybdenum-sulfide dimers of the present invention are designed for the production of polymeric forms of the molybdenum-sulfide dimers or of polymeric materials that are covalently linked to the molybdenum-sulfide dimers. Polymers may be produced from the vinyl containing dimers by processes well known to those of ordinary skill in the art. The monomer units may be used alone or with copolymers. The term prepolymer, as used herein, is to be interpreted to also include block co-polymers and as agents attached as a side chain on a polymer backbone.

In an additional embodiment of the present invention, it has been shown that the molybdenum-sulfide dimers will also react in the solid state with alkenes and alkynes. The solid state dimer, in either granular or powder forms, or as a thin film will react reversibly with alkenes and irreversibly with alkynes in much the same manner as in solution. This unanticipated result demonstrates that gas/solid separation/purification schemes may be performed utilizing the molybdenum-sulfide dimers of the present invention.

In one embodiment of the present invention, solid state films of the molybdenum-sulfide dimers are deposited on the surface of support materials and the supported solid state materials used in either batch or flow gas separation processes. In one embodiment, a solid supported molybdenum-sulfide dimer is contained in a column and used to remove alkynes from stream gases. After the dimer material has reached saturation by reaction with alkynes to form alkenedithiolate complexes, the unit holding the complexes can be treated by flowing H$_2$ at a slightly elevated temperature to release alkenes and return the molybdenum-sulfide dimer supported material to an active form to be used for further alkyne removal.

In a preferred embodiment of the invention, the support material is commercially available neutral alumina. The molybdenum-sulfide dimer may be placed on the aluminum support according to the procedures described in Example 6 below. Commercially available silica supports may also be utilized for this purpose.

According to the present invention, the molybdenum-sulfide dimers in solution may be used in a direct gas-liquid contactor or a membrane contactor. Under certain operating regimes and for certain separations, liquid/liquid contacting may also be utilized. There are a variety of methods for gas-liquid contacting; e.g., packed columns, open columns, and various staging approaches. As discussed above, a membrane contactor is a device in which the liquid phase is passed on one side of a membrane and the olefin phase is passed on the opposite side of the membrane. Mass transfer takes place across the membrane.

In a preferred embodiment of the invention, the molybdenum-sulfide dimers—in solid state, membrane supported or membrane incorporated forms—can be utilized in at least two areas in the conventional process utilized to produce ethylene and propylene from ethane and propane. The dimers may be used to replace the current alkyne removal module, and also as a chemically specific portion of a hybrid separation process for alkene separation or purification.

The following Examples, along with the skill and knowledge possessed by one of ordinary skill in the art, provides specific illustrations of the various aspects of the present invention.

EXAMPLE I

SYNTHESES OF IONIC WATER SOLUBLE MOLYBDENUM SULFIDE DIMERS WITH OLEFIN BINDING CAPABILITIES

The base or core structure of the molybdenum sulfide dimers may be modified by the introduction of substituents on the cyclopentadienyl or alkanedithiolate ligand positions. In one embodiment of the invention, the alkanedithiolate position may be altered according to the following reaction:

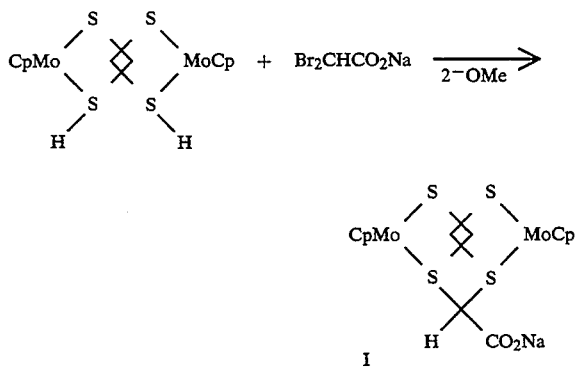

The dihydro-molybdenum sulfide dimer starting material was made according to the procedures described in Rakowski DuBois et al. *J. Am. Chem. Soc.*, vol. 102, pg. 7456 (1980). Reaction with the sodium or potassium salt of dibromoacetate and a base, preferably sodium methoxide, in tetrahydrofuran solvent at 25° C. for one hour led to the formation of the water soluble product 1. The reaction and resulting product must be protected from air. Following the reaction, solvent was removed and the product 1 was extracted with methanol and filtered through celite. Upon reduction of solvent, the product was obtained as a crystalline solid.

The structure of 1 is confirmed by proton NMR spectroscopy: $^1$H NMR (ppm in D$_2$O): 6.51, 6.39 (2s, Cp); 3.39 (s, CH). It has been shown that 1 reversibly binds with alkenes in water or alcohol solutions.

Derivatives of the molybdenum-sulfide dimers with water soluble substituents on the alkanedithiolate moiety were also prepared according to the following formula:

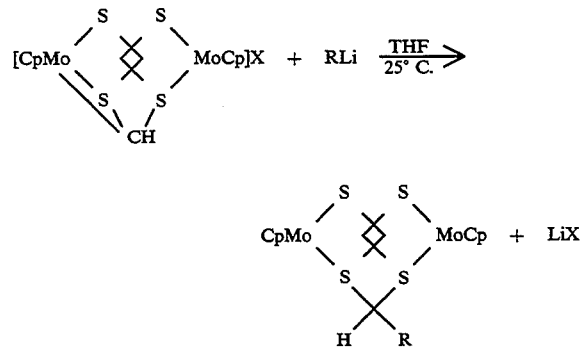

where MR=NaCH (CO$_2$CH$_3$)$_2$. In other embodiments, MR may be LiC(CH$_3$)$_2$CO$_2$Et or LiC(CH$_3$)$_2$CO$_2$Li. The starting material for this reaction 2, is prepared according to the procedures described in Birnbaum et al. *Organometallics*, vol. 9 pg. 156 (1990). Reaction with the nucleophiles occur at ambient temperatures in an organic solvent such as THF. Esters in the final products 3, may be hydrolyzed by conventional means to increase water solubility of the final products.

Further substitution of sulfide ligands in these structures can be accomplished with alkyl halides or acids, as shown below:

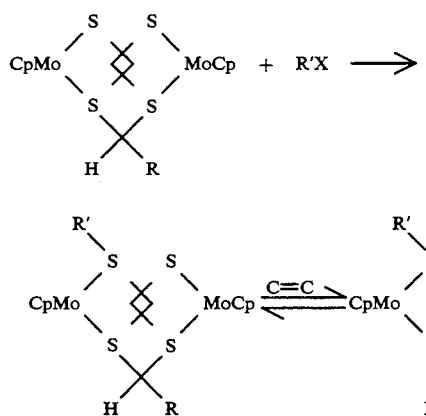

In some cases these cations retain the ability to interact reversibly with olefins.

A second class of water soluble molybdenumsulfide dimers consists of compounds where the cyclopentadienyl moieties have been modified. A procedure for synthesizing $[(C_5H_4CO_2Me)MoSC_2H_4S]_z$ is as described below:

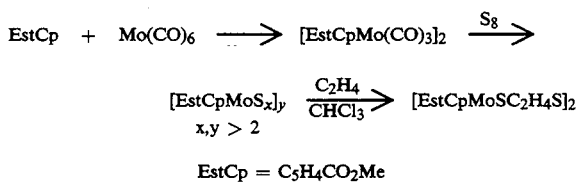

$EstCp = C_5H_4CO_2Me$

The esterified cyclopentadiene $C_5H_4CO_2Me$ is prepared according to the procedures described in Macomber et al. *Adv. in Organomet. Chem.*, vol. 21, pg. 1 (1982). This material is reacted with molybdenum carbonyl and sulfur, and then with ethylene. Reaction conditions are equivalent to those described for the synthesis of the homologous product with unsubstituted Cp ligands. See, Rakowski DuBois et al., *Inorg. Chem.*, vol. 20, pg. 3064 (1981). The ester substituted product 4 of this reaction was then hydrolyzed under basic conditions to produce the water soluble product 5 with carboxylate substituents as seen below:

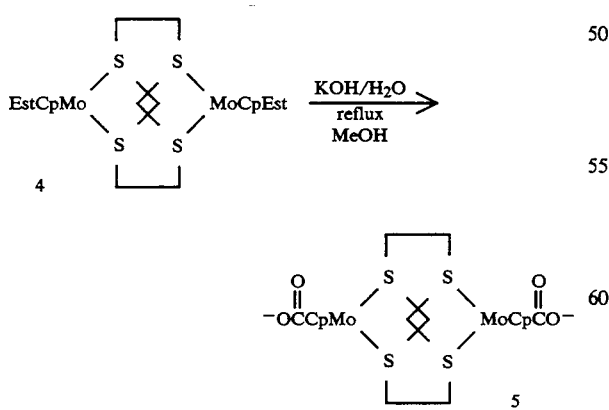

This water soluble product 5 has been characterized by NMR spectroscopy. $^1$H NMR (ppm in $D_2O$): 5.0, 5.2 (2 trip. Cp); 1.7 (s, $C_2H_4$). Dimer 5 may be thermally activated to release ethene under an active vacuum to form the water soluble dimer 6.

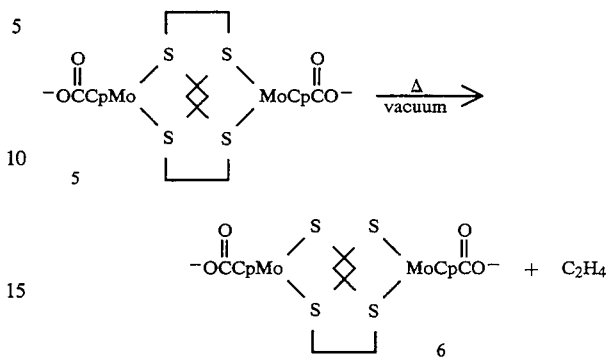

The water soluble molybdenum-sulfide dimer 6 may react reversibly with alkenes or form more stable adducts with alkynes according to the teachings of this invention.

The dimers 5 or 6 may also be used to prepare cationic derivatives by converting the ester substituent to amino substituted amides 7 by conventional organic amide synthesis; as would be familiar to those of ordinary skill in the art, as follows:

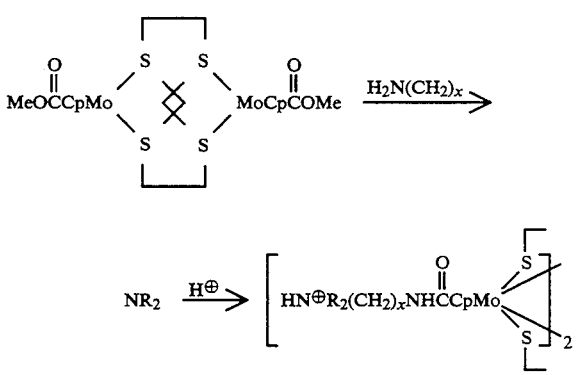

EXAMPLE 2

SYNTHESIS OF POLYMER PRECURSOR MOLYBDENUM-SULFIDE DIMERS WITH ALKENE BINDING CAPABILITIES

The introduction of an aldehyde substituent into the cyclopentadienyl ligand of the molybdenum-sulfide dimers of the present invention was accomplished as follows:

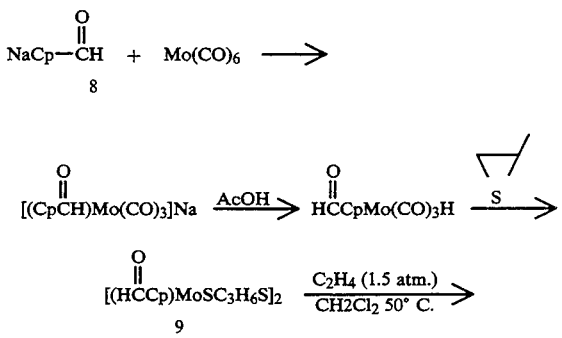

-continued

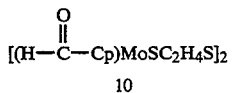
10

The free aldehyde cyclopentadienyl ligand 8 was prepared as described in Macomber et al. supra. The reaction to form the aldehyde substituted molybdenum-sulfide dimer 10 was then performed generally according to the procedures for synthesis of the unsubstituted molybdenum dimer as described in McKenna et al. supra and Rakowski DuBois et al. (1981) supra.

The propane dithiolate dimer 9 dissociates propene at 50° C. In the presence of excess ethylene, the thermal activation of 9 leads to the formation of dimer 10. Dimer 10 was isolated by chromatography of the thermal activation product mixture through an alumina column with a solution of 50:50 by volume $CH_3CN/CH_2Cl_2$. A first brown fraction was isolated by solvent removal and characterized as dimer 10 by NMR spectroscopy. $^1H$ NMR (ppm in $CDCl_3$): 5.35 (s, Cp), 9.29 (s, CHO); 1.90 (s, $C_2H_4$). A second fraction eluted from the column was shown to be the mono-aldehyde 11.

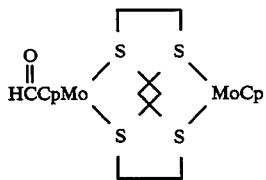
11

Dimer 11 was also characterized by NMR spectroscopy. $^1H$ NMR ($DCCl_3$): 5.28, 5.26 (2 trp. Cp CHO); 5.10 (s, Cp); 9.25 (s, CHO); 1.8, 1.9 (m, $C_2H_4$).

The aldehyde substituted molybdenum-sulfide dimers 10, 11, may be reacted with methylenetriphenylphosphorane to lead to the formation of vinyl substituted dimers, as shown below.

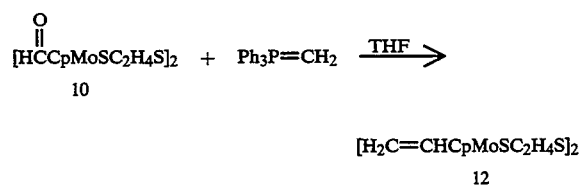

The vinyl forming reaction may be performed generally according to the procedures described for other aldehyde Cp systems, see for example Rausch et al., *J. Organometallic Chem.*, vol. 205, pg. 353 (1981). The vinyl derivatives may then be converted into polymeric materials as a co-polymer or monomer unit by redox or other well known polymerization formation processes. The polymeric molybdenum-sulfide dimer compounds may be used in the solid state separately or as supported materials, or may be used in membrane synthesis to form membrane materials containing the molybdenum-sulfide dimer functionality.

EXAMPLE 3

OLEFIN INTERACTIONS WITH MOLYBDENUM-SULFIDE DIMERS AND OLEFIN SEPARATIONS

Equilibrium constants for the following reaction were determined by NMR spectroscopy.

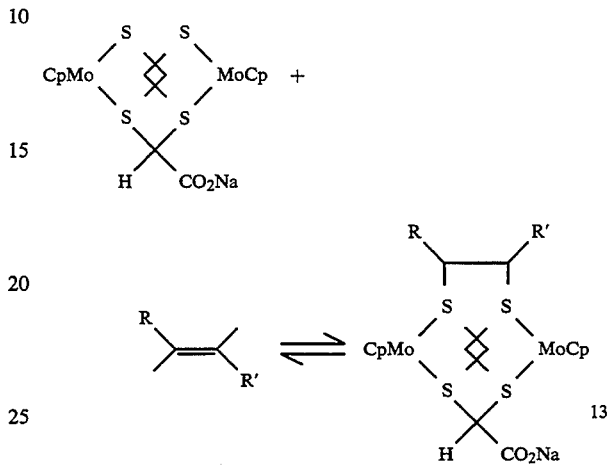

A small excess of olefin was added to an aqueous ($D_2O$) solution of 1 of known concentration in an NMR tube, and the tube flame sealed. NMR integrations were determined for resonances corresponding to each compound in solution at periodic intervals (over 0.5 to 5 days) until relative concentrations of 1 and 13 remained constant. Equilibrium ratios were calculated using the integration ratios and the known initial concentration of dimer 1.

Equilibrium constants for an extensive series of molybdenum-sulfide dimers can be seen in Table II. For selected cases, the olefin complexation reactions were carried out in either aqueous or non-aqueous solutions in the presence of at least about one equivalent of $H_2S$ per equivalent of molybdenum-sulfide dimer. No inhibition of the interaction with olefins was detected in the presence of the $H_2S$.

To demonstrate the principle of alkene separations using the molybdenum-sulfide dimers as olefin transport agents in an aqueous liquid membrane, a simple experimental apparatus 18, such as depicted in FIG. 1, may be used. An olefin mixture may be dissolved in an organic solvent in section 20. Aqueous solution containing the molybdenum-sulfide dimer is held in the middle lower section of the apparatus 22, and is stirred mechanically. Organic solvent is also found in section 24 of the apparatus. The concentration gradient of olefin in organic solvent 24 can then be monitored periodically by gas liquid chromatography.

In reactions of dimers with olefin mixtures, selective complexation of the less sterically hindered olefin by the molybdenum-sulfide dimer is favored as shown in the equilibrium constant studies. Rates of olefin complexation to the sulfide ligands are known to be rapid. See DuBois et al. *J. Am. Chem. Soc.* vol. 103, pg. 3429 (1981). These experiments will indicate the rates of olefin dissociation.

EXAMPLE 4

INTERACTIONS OF MOLYBDENUM-SULFIDE DIMERS WITH ALKYNES

A number of the modified molybdenum-sulfide dimers of the present invention were shown to undergo reactions with alkynes in a manner analogous to that shown for the unmodified dimers. See, McKenna et al. supra; Rakowski DuBois et al. supra. For example, dimer:

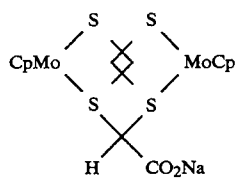

in $CD_3OD$ in the presence of three equivalents of acetylene at room temperature reacted almost immediately to form the alkenedithiolate. The alkenedithiolate product $(MeCpMo)_2$ $(S_2CHCO_2^-)(SC_2H_2S)$ was identified by NMR spectroscopy. $^1$H NMR: ($CD_3OD$): 6.86 (s,$S_2CHCO_2^-$); 6.56 (s,$S_2C_2H_2$); 5.69, 5.60 (m, Cp); 2.09, 1.98 (2s, MeCp).

In a similar experiment the diethanedithiolate modified dimer

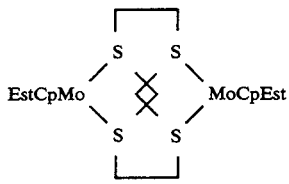

was reacted with excess phenyl acetylene in $CHCl_3$ as shown below:

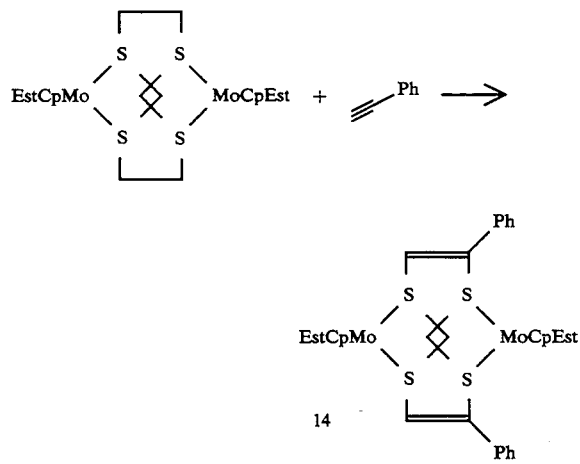

Again, the product was identified by NMR spectroscopy in $CDCl_3$. $^1$H NMR: 7.2 (m,Ph); 6.65 (s, C=CH); 6.15, 5.9 (2t, Cp); 3.15 (s, OMe).

A modified alkene dithiolate dimer was reacted with hydrogen at 25° C. as shown below.

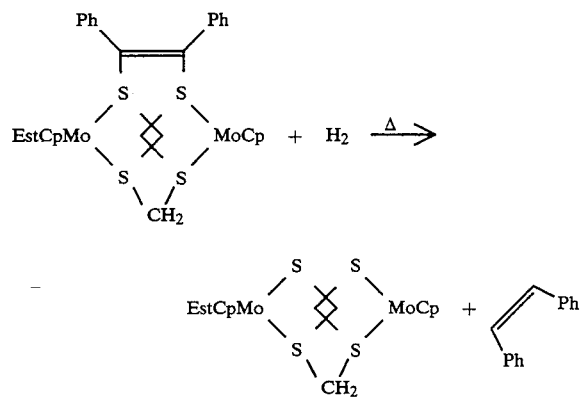

This reaction, with the $H_2$ at a pressure of 150 mm, was substantially completed in three days. The analogous reaction using the alkenedithiolate with both Cp groups containing esters took 23 days to reach completion. The reduction step of the molybdenum-sulfide dimer alkyne adduct to yield the dimer used to "trap" the alkyne is important in providing a reusable system for alkyne removal.

EXAMPLE 5

MEMBRANE SUPPORTED COMPLEXES

Cationic molybdenum complexes were incorporated into NAFION ion exchange membranes of varying degrees of thickness. For example, when a sample of NAFION (25 μM thickness) is soaked in a $10^{-2}$M methanol solution of $[(C_5H_5Mo)_2(S_2CH_2)(\mu\text{-}S)(\mu\text{-}SCMe_3)]^+$ 15, for 15–30 min., the membrane takes on the purple color of the cationic complex. The amount of 15 incorporated into the NAFION membrane was determined by measuring the change in concentration of 15 in the methanol solution (by visible absorption spectrometry) and by measuring the mass change of the membrane resulting from the ion exchange process. (Calculations from both methods indicated that 45% of the sodium ions in the original membrane had exchanged with the molybdenum cation.) Similar experiments were carried out with other thicknesses of ion exchange membrane and with other cationic complexes of the formula $[(CpMo)_2(S_2CH_2)(\mu\text{-}S)(\mu\text{-}SR)]^+$.

| R | Nafion Thickness | % Loading |
| --- | --- | --- |
| $CMe_3$ | 25 uM | 45 |
| $CMe_3$ | 175 uM | 35 |
| $CH(Me)CO_2H$ | 25 uM | 41 |

In a similar procedure, the anionic complex 1 has been exchanged into a Raipore anion exchange membrane. The manipulations of 1 and its substituted membrane however must be carried out in an air-free environment.

In $CH_2Cl_2$ solution, 15 interacts reversibly with ethene with a $K_{eq}=95$ at 20° C. as shown below:

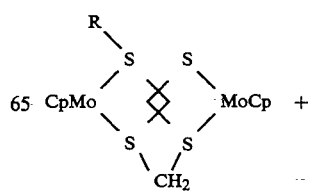

-continued

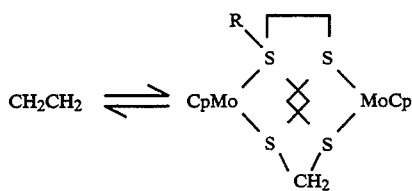

K$_{eq}$ for the interaction of 15 with propene is 5 at 20° C. The complex does not react with alkanes. On the basis of this behavior of the cation in solution, it is seen that the cation-substituted membrane will function as an efficient device for separating ethene from propene, and for separating ethene from saturated hydrocarbons.

EXAMPLE 6

Reactions of Molybdenum Complexes in the Solid State with Alkenes and Alkynes

A solid sample of (C$_p$Moμ-S)$_2$S$_2$CH$_2$ was found to react reversibly with olefins. For example, when two equivalents of ethene were added to a solid sample of the molybdenum complex at room temperature, a gradual color change to brown was observed. After three days, the unreacted ethene was removed and the solid was dissolved in CDCl$_3$. The $^1$H NMR spectrum of this sample showed that ca. 75% of the solid had been converted to the ethanedithiolate complex. The solvent was removed from the sample and the solid material was heated at 50° C. under vacuum for two days. The NMR spectrum of the resulting product indicated that 82% of (CpMoμ-S)$_2$S$_2$CH$_2$ had been reformed by dissociation of ethene. The interaction of a thin film of (CpMoμ-S)$_2$S$_2$CH$_2$ with olefins has also been monitored by visible spectroscopy.

Alumina Supported Complexes. The complex (CpMoμ-S)$_2$S$_2$CH$_2$ has been absorbed on neutral alumina (100 mesh) by the following procedure. A 10$^{-3}$ M solution of the complex in CH$_2$Cl$_2$ (25 mL) was added to 5 g of alumina and the solvent from this slurry was evaporated on a rotary evaporator. The resulting alumina became light blue, indicating that the blue molybdenum complex had been absorbed.

The solid state absorbed complexes retain their reversible reactivity with olefins. This has been demonstrated by admitting an atmosphere of a gaseous olefin (ethane, propene, or butenes) to a layer of molybdenum treated alumina. A color change on the surface of the alumina from blue to brown was observed within seconds. The color change is analogous to that observed for olefin adduct formation in solution. The alumina containing the absorbed molybdenum sulfide-olefin adduct was subjected to thermal desorption analysis. The thermal desorption curves indicated that olefins were desorbed over narrow temperature ranges (1°-2°). For example, propene was desorbed at 72° C. and trans-2-butene at 83° C. The identity of the desorbed species was confirmed by mass spectroscopy. The absorption and desorption of olefins was repeated in multiple cycles without notable degradation of the absorbed molybdenum complex.

The dried alumina treated with (CpMoμ-S)$_2$S$_2$CH$_2$ also reacted with an atmosphere of acetylene as indicated by a color change on the alumina surface from blue to brown. The coordinated acetylene was not released thermally at temperatures up to ca. 100° C. However, addition of hydrogen to the alumina surface heated at 70° resulted in a slow conversion of the absorbed molybdenum complex back to the blue derivative (C$_p$Moμ-S)$_2$S$_2$CH$_2$. The reaction appears to be analogous to that observed in solution.

We claim:

1. A method of separating alkenes or alkynes from a hydrocarbon mixture by use of differential binding rates or equilibrium constants of said alkenes or alkynes to a molybdenum-sulfide dimer comprised of the formula:

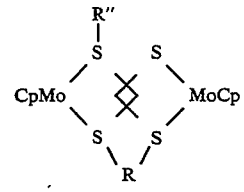

wherein Cp is selected from the group consisting of: —C$_5$H$_5$, —C$_5$H$_4$CH$_3$, —C$_5$H$_4$CO$_2$CH$_3$, —CH$_5$H$_4$CO$_2$Na, —C$_5$H$_4$CH═CH$_2$, —C$_5$(CH$_3$)$_5$, or C$_5$H$_4$CHO, R is selected from the group consisting of —C$_2$H$_4$ or —CHR', wherein R' is selected from the group consisting of H, —CO$_2$Na, —CO$_2$CH$_3$, —C(CH$_3$)$_2$CO$_2$Et, —C(CH$_3$)$_2$CO$_2$Li or —CH(CO$_2$CH$_3$)$_2$, and R" is selected from the group consisting of —C(CH$_3$)$_3$, —CH(CH$_3$)CO$_2$H, or nothing, such method comprised of the steps:
preparing said molybdenum sulfide-dimer;
contacting said hydrocarbon mixture with said molybdenum-sulfide dimer, wherein alkenes or alkynes having an increased affinity to the molybdenum-sulfide dimer relative to the hydrocarbon mixture may be separated from the remainder of the hydrocarbon mixture;
separating the increased affinity alkenes or alkynes from the remainder of the hydrocarbon mixture.

2. The method of claim 1 wherein said hydrocarbon mixture comprises a plurality of alkenes.

3. The method of claim 1 wherein said hydrocarbon mixture comprises isomeric alkenes of the same molecular formula.

4. The method of claim 1 wherein said hydrocarbon mixture comprises a plurality of alkenes and a plurality of alkanes.

5. The method of claim 1 wherein said hydrocarbon mixture comprises a plurality of alkynes and a plurality of alkanes.

6. The method of claim 1 wherein said hydrocarbon mixture comprises a plurality of alkynes and a plurality of alkenes.

7. The method of claim 1 wherein said hydrocarbon mixture contains alkynes.

8. The method of claim 1 wherein said hydrocarbon mixture contains H$_2$S.

9. The method of claim 1 wherein said molybdenum-sulfide dimer is attached to a permselective membrane.

10. The method of claim 9 wherein said membrane is an ion-exchange membrane.

11. The method of claim 9 wherein said molybdenum-sulfide dimer is covalently incorporated into the polymeric matrix of said membrane.

12. The method of claim 1 wherein said molybdenum-sulfide dimer is on the surface of a solid support.

13. The method of claim 1 wherein said molybdenum-sulfide dimer is in an aqueous solution.

14. The method of claim 13 wherein said molybenum-sulfide dimer is water soluble.

15. A method for removing alkynes from a gaseous hydrocarbon feed stream by use of differential binding rates or equilibrium constants of such compounds to a molybdenum-sulfide dimer comprised of the formula:

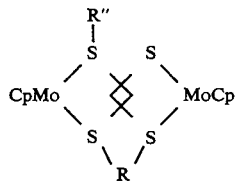

wherein Cp is selected from the group consisting of: $-C_5H_5$, $-C_5H_4CH_3$, $-C_5H_4CO_2CH_3$, $-C_5H_4CO_2Na$, $-C_5H_4CH=CH_2$, $-C_5(CH_3)_5$, or $-C_5H_4CHO$, R is selected from the group consisting of $-C_2H_4$ or $-CHR'$, wherein R' is selected from the group consisting of H, $-CO_2Na$, $-CO_2CH_3$, $-C(CH_3)_2CO_2Et$, $-C(CH_3)_2CO_2Li$ or $-CH(CO_2CH_3)_2$, and R" is selected from the group consisting of $-C(CH_3)_3$, $-CH(CH_3)CO_2H$, or nothing such method comprised of the steps:

preparing said molybdenum sulfide-dimer;

contacting said hydrocarbon feed stream with said molybdenum-sulfide dimer, wherein alkynes having an increased affinity to the molybdenum-sulfide dimer relative to the hydrocarbon feed stream may be separated from the remainder of the hydrocarbon feed stream;

separating the increased affinity alkynes from the remainder of the hydrocarbon feed stream.

16. The method of claim 15 further comprised of the step: heating said increased affinity alkynes of said molybdenum-sulfide dimer in the presence of hydrogen to release the alkyne and the molybdenum sulfide dimer.

* * * * *